United States Patent

Kiske et al.

[11] Patent Number: 5,119,810
[45] Date of Patent: Jun. 9, 1992

[54] VENTILATING APPARATUS THAT MAINTAINS LOW/CONSTANT COMPLIANCE

[75] Inventors: Siegfried Kiske, Gross Grönau; Carl F. Wallroth; Wolfgang Sauer, both of Lübeck, all of Fed. Rep. of Germany

[73] Assignee: Drägerwerk Aktiengesellschaft, Lübeck, Fed. Rep. of Germany

[21] Appl. No.: 461,288

[22] Filed: Jan. 5, 1990

[30] Foreign Application Priority Data

Jan. 7, 1989 [DE] Fed. Rep. of Germany ....... 3900276

[51] Int. Cl.$^5$ .................. A61M 16/00; A62B 7/04; F16K 31/26
[52] U.S. Cl. .................. 128/204.26; 128/204.22; 128/203.12; 128/205.23
[58] Field of Search ............. 128/204.21, 204.26, 128/204.27, 204.28, 205.12, 205.13, 205.14, 205.17, 205.18, 204.22, 204.23, 205.23, 203.12

[56] References Cited

U.S. PATENT DOCUMENTS

| | | | |
|---|---|---|---|
| Re. 25,871 | 10/1965 | Andreasen | 128/204.28 |
| 3,961,627 | 6/1976 | Ernst et al. | 128/204.21 |
| 4,022,234 | 5/1977 | Dobritz | 128/205.11 |
| 4,150,670 | 4/1979 | Jewett et al. | 128/204.27 |
| 4,245,633 | 1/1981 | Erceg | 128/205.17 |
| 4,453,543 | 6/1984 | Kohnke et al. | 128/205.12 |
| 4,550,726 | 11/1985 | McEwen | 128/204.23 |
| 4,552,141 | 11/1985 | Torri | 128/205.12 |
| 4,579,115 | 4/1986 | Wallroth et al. | 128/204.21 |
| 4,611,590 | 9/1986 | Ryschka et al. | 128/203.14 |
| 4,838,259 | 6/1989 | Gluck et al. | 128/204.21 |
| 4,905,685 | 3/1990 | Olsson et al. | 128/203.12 |

FOREIGN PATENT DOCUMENTS 0121255 10/1984 European Pat. Off. ....... 128/205.12

OTHER PUBLICATION

The United States Patent Quarterly, 42 US PQ, p. 526-28, The Bureau of National Affairs, Inc., Wash., D.C. Sep. 9, 1955.

Primary Examiner—Edgar S. Burr
Assistant Examiner—Kimberly L. Asher
Attorney, Agent, or Firm—Walter Ottesen

[57] ABSTRACT

The invention is directed to a ventilating apparatus including a ventilating device and a closed breathing circuit wherein fresh gas is metered by means of a controller via a fresh gas line. A reservoir having a changeable volume is connected to the fresh gas line. In this way, at least the quantity of respirating gas which is consumed is again replenished. This arrangement is improved such that a very small quantity of respirating gas can be metered with the compliance of the entire system being low and remaining necessarily constant. With the invention, a system is obtained which is easy to control with the smallest possible configuration and least complex measuring sensors. For this purpose, a reservoir connected downstream of the metering unit is branched off of the fresh gas line and is provided with a level indicator. The signal of the level indicator indicates the level and is supplied as an actual value to the controller and compared to a pregiven desired value. A cutoff device is interposed ahead of the location at which the fresh gas line communicates with the breathing circuit.

4 Claims, 1 Drawing Sheet

VENTILATING APPARATUS THAT MAINTAINS LOW/CONSTANT COMPLIANCE

FIELD OF THE INVENTION

The invention relates to a ventilating apparatus having a closed breathing circuit or a semi-closed breathing circuit. The gaseous components required for the ventilation are metered into the breathing circuit via a fresh gas line whereby at least the consumed respirating gas is again replenished.

BACKGROUND OF THE INVENTION

Ventilating apparatus having a closed breathing circuit are preferably utilized in anesthesia treatment because this kind of apparatus configuration assures that the following can be realized: a smallest possible consumption of fresh gas (for example, respirating gas enriched with oxygen); or a smallest possible consumption of anesthetic gases and anesthetic agents; and, maintaining respirating gas moisture and respirating gas temperature during an anesthesia. Carbon dioxide is removed from the respirating gas exhaled by the patient and the consumption of, for example, oxygen and possibly anesthetic gas is compensated by metering fresh gas. For this purpose, it is necessary only to meter so much fresh gas as corresponds to the actual consumption and leakage which possibly occurs.

In contrast and for ventilating apparatus having a semi-closed breathing circuit, only a portion of the breathing gas exhaled by the patient is again returned. For this purpose, the fresh gas flow is adjusted substantially higher than the actual consumption which effects a thinning of the exhaled respirating gas. The excess consists of a mixture of fresh gas and exhaled respirating gas. This excess is vented via a valve after each breath. The excess gas therefore is lost and must be eliminated by means of complex removal devices such as a suction device. The venting of excess gas also results in an excessive consumption of anesthetic gases and anesthetic agents.

A closed circuit anesthesia apparatus is disclosed in European Patent 0 121 255 and uses a complex control loop for metering fresh respirating gas. The respirating gas components are replenished in the control loop with corresponding sensors which are used for driving the metering unit. In this way, the level of the loop conducting the respirating gas is determined at every instant during a ventilation and the required quantity of fresh gas together with the anesthetic gas is supplied.

A metering of this kind is however complex and expensive since a measuring sensor is needed for each gaseous component present in the composition making up the respirating gas so that after a completed measurement, the corresponding quantity of respirating gas can again be resupplied. In a closed breathing circuit, only several 100 ml of respirating gas are used for each breath; but the entire respirating gas system has a substantially greater content with respect to its volume. For this reason, for a precise metering of such small quantities it is required that the compliance changes as little as possible in the course of a ventilation. An increased compliance would have as a consequence that only a small metered quantity would correspond to that which was actually consumed and the excess would actually increase the pressure in the breathing system.

A compliance change of this kind is facilitated in the known ventilating system in that a reservoir having a changing volume is continuously connected to the breathing gas line during the entire breathing cycle whereby its content changes in accordance with consumption. A further volume change occurs because the elastic components such as the breathing hoses in the breathing loop are increased with respect to their volume because of the ventilating pressure. This effect is especially noticeable during the inspiration phase. The metering of the consumed respirating gases thus takes place in a breathing circuit of variable compliance.

SUMMARY OF THE INVENTION

It is an object of the invention to improve a ventilating apparatus of the kind described above such that even the metering of very small quantities of respirating gas is made possible while a low compliance of the overall system remains necessarily constant. This is achieved by providing an apparatus which is simple to control and which has the smallest possible complexity and the least complex sensing system. Losses of fresh gas or anesthetic agents occurring as a consequence of operation are intended to be minimized.

In the first embodiment of the invention, the ventilating apparatus includes a closed breathing loop. According to a feature of this embodiment of the invention, a reservoir is connected downstream of the metering unit and is connected on a branch which branches off of the fresh gas line. The reservoir is provided with a level indicator which supplies an actual signal to a controller which is indicative of the level of the reservoir. This actual signal is compared with a pregiven desired value and a cutoff device is interposed ahead of the opening of the fresh gas line into the breathing loop.

In another embodiment of the invention, the ventilating apparatus includes a semi-closed breathing loop and in this embodiment, the respirating gas pump unit is provided with a pressure-measuring device as a level indicator for the respirating gas in the breathing loop. The signal of the level indicator is compared with a pregiven desired value at the controller. In addition, a relief valve is provided in the breathing circuit and is connected to the controller.

The advantage of the invention is that the metering unit can be decoupled from the breathing circuit proper by means of the cutoff device and be connected to the breathing circuit only when required during the expiration cycle of the ventilation in order to take that quantity of fresh gas from the reservoir filled with fresh gas which must be replaced because of previous consumption.

The quantity of fresh gas taken from the reservoir corresponds to this consumption and the operator of the apparatus can determine the consumption on the quantity taken and correspondingly refill the reservoir with fresh gas. The inspiration cycle can take place with always constant compliance when the metering unit is separated and the reservoir is blocked. The reservoir is only connected with the breathing circuit during exhalation so that the ventilating apparatus takes the exhaled air as well as the volume consumed and needed for refilling the ventilating stroke. Thereafter, the metering unit is again cut off and a subsequent inspiration is carried out by the ventilating apparatus with the inhalation stroke volume which necessarily corresponds thereto. It is advantageous to determine the content via a level indicator so that the operator of the apparatus can easily recognize when the reservoir must again be refilled by the metering unit.

An especially simple and easy to operate embodiment is realized in that a balloon-like expansion chamber is connected to the respirating gas line via a branch line with a pressure sensor in the form of a level indicator being provided for taking a reading also at the branch line.

In a semi-closed breathing circuit, it is advantageous to provide the respirating gas pump unit with a level indicator in the form of a pressure-measuring device for the quantity of respirating gas in the breathing circuit and to provide a relief valve in the breathing circuit. The quantity of breathing gas in the breathing circuit is limited by the relief valve and an unwanted increase in pressure is prevented. The metering of the fresh gas thus takes place in a breathing circuit having an approximately constant respirating gas volume.

The relief valve is closed during the inspiration phase and is only open during the expiration phase when the fresh gas flow flowing into the breathing circuit is greater than the gas lost because of the consumption by the patient or because of leakage. In this case, the end expirative pressure increases. This pressure is measured with the pressure-measuring device at the respirating gas pump unit and if this pressure exceeds a preselected upper pressure limit, then the relief valve is opened. The relief valve is again closed if the pressure drops below a preselected lower pressure limit. The relief valve can remain closed over several breathing strokes in accordance with the selection of the pressure limits and the adjusted fresh gas flow. In this manner, the advantages of the closed breathing circuit can be utilized to a large extent in a semi-closed breathing circuit. These advantages are the following: a high utilization of fresh gas and, a good moisturization and warming of the inspiration gases. The relief valve is opened after each breath when the fresh gas flow is adjusted to a high level.

The metering unit, the level indicator, the cutoff device and the ventilating apparatus with its respirating gas pump unit should be connected to a common controller if, for a closed breathing circuit, the metering is not to take place manually and if it is intended that the operator be relieved of the task of monitoring the level of the reservoir. The metering can then take place automatically for each breathing cycle simply by metering the quantity of respirating gas consumed in each instance or, as in the case of known embodiments, the metering can take place after a desired number of breathing strokes by metering the respirating gas quantity consumed in the meantime provided that the content of the reservoir is adequate. If the capacity of the reservoir is adequate, then even for larger breathing strokes which suddenly become necessary, the larger respirating gas requirement necessary can be provided from the content of the reservoir. With the metering unit being cut off, the then empty reservoir can be refilled during the inhalation cycle. Its content is then again available for the subsequent ventilating strokes.

For a semi-closed breathing circuit, the quantity metered is adjusted to a preferably constant value and stored in the reservoir. The cutoff valve and the vent valve are closed during the inhalation cycle and the respirating gas pumping unit carries out a breathing stroke. The expiration phase is initiated by opening the cutoff valve whereupon fresh gas from the reservoir and a portion of the expiration gas of the patient reaches the expanding chamber of the respirating gas pump unit.

The relief valve opens at the end of the expiration phase if the upper pressure limit inputted to the controller is exceeded.

The relief valve is closed if the pressure measured by the pressure-measuring device remains within the preselected limits. Losses of fresh gas or anesthetic agents caused by operation are minimized in this manner. In addition, the metering of fresh gas into the breathing circuit can be influenced by the controller.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
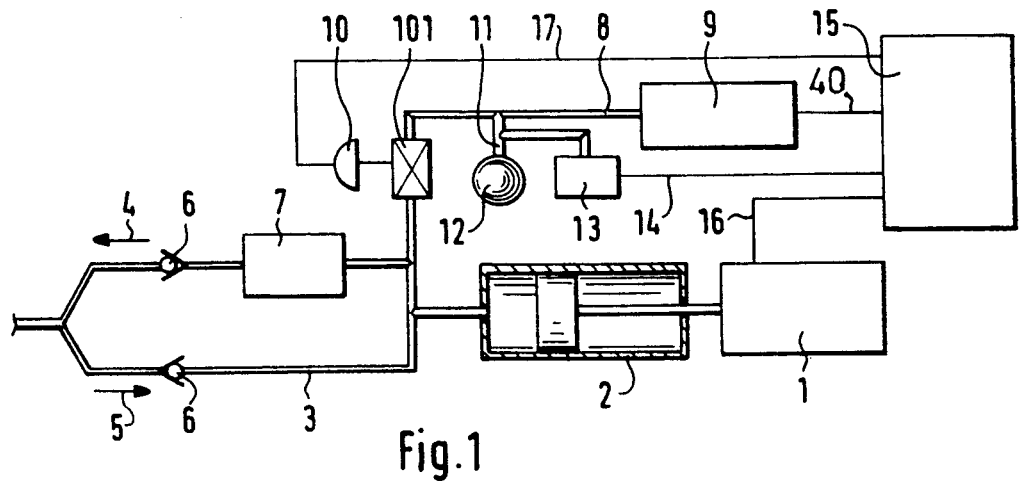
FIG. 1 is a block diagram showing a first embodiment of the ventilating apparatus according to the invention with a closed breathing circuit; and, FIG. 2 is a second embodiment of the ventilating apparatus according to the invention with a semi-closed breathing circuit.

In FIG. 1, a ventilating device 1 includes a pump unit 2 which can be configured, for example, as the combination of a cylinder with a piston sliding therein. The ventilating device 1 with pump unit 2 is connected to a closed breathing circuit 3. The breathing circuit 3 pumps the respirating gas to the patient (not shown) during the inspiration (inspiration arrow 4) and moves the respirating gas back to the pump unit 2 during expiration (expiration arrow 5). The circulation of the respirating gas is maintained by the pump unit 2 and is held in the circuit represented by arrows (4, 5) by the directional valves 6. A carbon dioxide absorber 7 is disposed in the breathing circuit 3 for purifying the respirating gas.

Respirating gas which is consumed during the ventilating cycle or which escapes through possible leaks is resupplied to the breathing circuit 3 via a fresh gas line 8. For this purpose, a metering unit 9 and an electrically actuable cutoff valve 101 are connected into the fresh gas line 8. A branch line 11 is provided to connect into the fresh gas line 8 between the metering unit 9 and the valve 101. A balloon having a changeable volume acts as a reservoir 12 and is connected to the branch line 11. A pressure sensor configured as a level indicator 13 is connected into the branch line 11. The pressure signal supplied by the pressure sensor is supplied via a signal line 14 to a controller 15.

A control line 16 is connected from the controller 15 to the pump unit 2 and a valve signal line 17 is connected from the controller 15 to the control component 10 of the cutoff valve 101. Likewise, a control line 40 begins at the controller 15 and extends to the metering unit 9. In this way, the controller 15 provides the possibility to control the supply of fresh gas from a fresh gas source which can, for example, be integrated into the controller 15.

With respect to the operation of the ventilating device 1 together with the breathing circuit 3 and the components corresponding thereto, it is assumed in FIG. 1 that the piston of the pump unit 2 is just in the process of an inspiration stroke in accordance with inspiration arrow 4. During this inspiration stroke, the valve 101 is closed by the controller 15 and the reservoir 12 is filled with fresh gas. The pressure sensor 13 registers a corresponding inner pressure of the balloon 12 and supplies this inner pressure to the controller 15 as a measuring signal.

After the inspiration stroke has ended, the pump unit 2 announces to the controller 15 the reversal into the expiration stroke according to expiration arrow 5 via the control line 16 so that now the exhaled air from the breathing circuit 3 flows into the volume of the pump unit which increases as the piston moves through its return stroke. At the same time, the valve 101 is opened via the valve signal line 17 so that the returning piston of the pump unit 2 additionally draws fresh gas into the breathing circuit 3 from the reservoir 12 if the stroke volume during the expiration stroke cannot be provided adequately from the breathing circuit 3. In this case, the patient (not shown) has consumed respirating gas or, in addition, leaks have developed through which the respirating gas has been lost to the ambient during the preceding inspiration stroke. After the expiration stroke is completed, this condition is announced by the ventilating device 1 to the controller 15 whereupon the reversal into the inspiration stroke takes place and the cutoff valve 101 is closed at the same time.

In the closed position of the fresh gas line, the reservoir 12, which has been partially or entirely emptied, is filled with fresh gas via the metering unit 9 and this filling process continues until the level indicator 13 indicates the previously specified pressure monitored by the controller 15. At this point in time, the controller cuts off the fresh gas supply via the metering unit 9 and the filled balloon 12 is available so that the latter can be tapped during the next expiration stroke of the pump unit 2.

Figure 2:
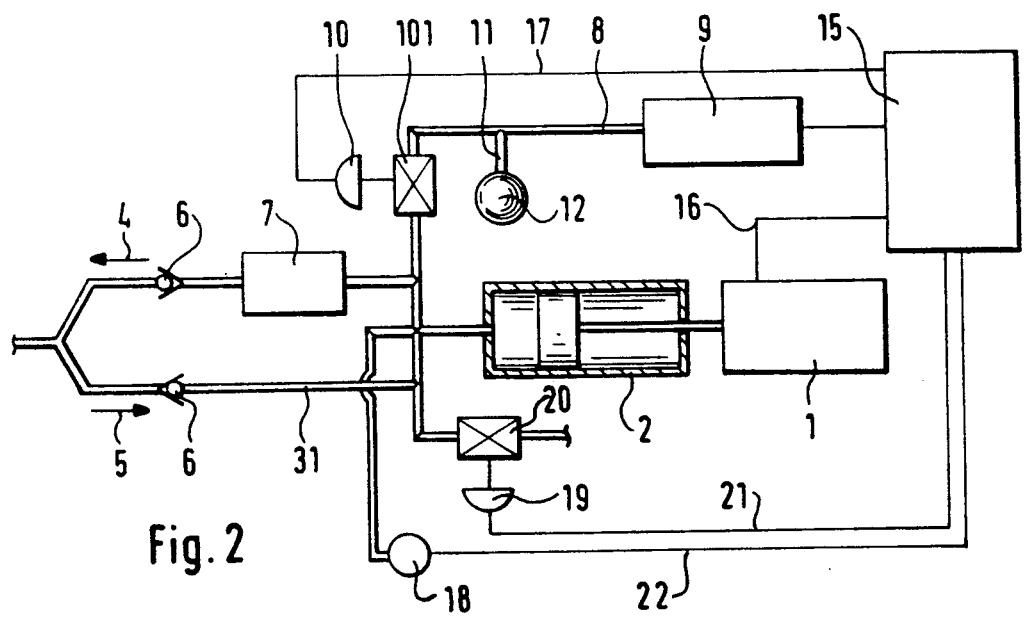

In FIG. 2, a ventilating apparatus 1 is illustrated with a semi-closed breathing circuit 31. The components in FIG. 2 are provided with the same reference numerals as in FIG. 1 insofar as the components are the same. A pressure-measuring device 18 is connected to the pump unit 2 and functions as a level indicator for the quantity of respirating gas in the breathing circuit 31. An electrically drivable relief valve 20 is provided which is connected to the controller 15 via a control component 19 and a signal line 21. The pressure-measuring device 18 is connected to the controller 15 via a signal line 22.

With respect to the operation of the ventilating apparatus 1 together with the breathing circuit 31 and the components illustrated in FIG. 2, it is assumed that the pump unit 2 is just in the process of an inspiration stroke according to the inspiration arrow 4. The metering unit 9 is adjusted to a constant fresh gas flow of, for example, 4 L/min. The cutoff valve 101 is closed so that the fresh gas flows into the reservoir 12. The relief valve 20 in the semi-closed breathing circuit 31 is likewise closed. During the inspiration stroke, the piston of the pump unit 2 moves the respirating gas to the patient.

The cutoff valve 101 is open with the initiation of the expiration phase (expiration arrow 5). Respirating gas flows out of the reservoir 12 and the breathing circuit 31 into the pump unit 2 because of the piston of the pump unit 2 which undergoes its return stroke. The pressure in the breathing circuit 31 is continuously measured at the pump unit 2 with the pressure-measuring device 18 and, at the end of the expiration phase, is compared to an upper pressure limit likewise preselected at the controller 15. If the pressure exceeds this upper pressure limit (for example, 1 mbar), then the relief valve 20 is opened and a portion of the respirating gas is vented to the ambient. A lower pressure limit such as 0.5 mbar is likewise preselected at the controller 15. When this lower pressure limit is reached, the relief valve 20 is closed. Thereafter, a new inspiration stroke can be carried out. If the pressure measured by the pressure-measuring device 18 remains below the upper pressure limit, then the relief valve 20 remains closed. The relief valve 20 can remain closed even for several ventilating strokes in accordance with the fresh gas quantity adjusted at the metering unit 9 provided that the inflowing fresh gas quantity is approximately the same as the quantity of gas taken up by the patient and lost through leakage. By opening the relief valve 20 as required, losses of fresh gas or anesthetic agents associated with operation are minimized and the advantages of a completely closed breathing circuit 3 (without a relief valve) are maintained even for a semi-closed breathing circuit to a large extent. These advantages include the high fresh gas utilization and the good moisturization associated therewith as well as the warming of the inspiration gases.

The invention is not limited to the ventilation with fresh gas alone; instead, several volatile anesthetic agents can be admixed to the fresh gas which, together with the additional oxygen, can be metered in the same manner into the breathing circuit (3, 31).

It is understood that the foregoing description is that of the preferred embodiments of the invention and that various changes and modifications may be made thereto without departing from the spirit and scope of the invention as defined in the appended claims.

What is claimed is:

1. A ventilating apparatus comprising:

a closed breathing circuit for pumping respiratory gas to a patient during inspiration and for moving the respiratory gas away from the patient during expiration;

a fresh gas line connected to said breathing circuit for conducting fresh gas into said breathing circuit with said fresh gas containing gaseous components needed for ventilating the patient;

a metering unit for metering said fresh gas into said fresh gas line;

means for providing constant compliance during said inspiration, said means including a cutoff valve mounted in said fresh gas line between said breathing circuit and said metering unit so as to be downstream of said metering unit;

said cutoff valve being switchable between a closed position wherein said fresh gas line is cut off from said breathing circuit and an open position wherein said fresh gas line is open to said breathing circuit;

changeable volume reservoir means connected into said fresh gas line downstream of said metering unit and upstream of said cutoff valve for receiving said fresh gas therein when said cutoff valve is in said closed position;

level sensing means disposed at said reservoir means for sensing the level of fresh gas in said reservoir means and for providing an actual value signal indicative of said level;

a controller for receiving said actual value signal and comparing said actual value signal to a pregiven desired value signal and for cutting off the supply of said fresh gas via said metering unit when the level of fresh gas in said reservoir means corresponds to said desired value signal;

means for determining the beginning and end of said expiration and for providing respective first and second signals indicative of said beginning and said end of said expiration; and, said controller being connected to said cutoff valve for switching said cutoff valve into said open position in response to said first signal so as to permit said reservoir means to supply fresh gas stored therein to said breathing circuit in a quantity sufficient to replace the respirating gas consumed by the patient and/or lost because of possible leaks in the apparatus and to then switch said cutoff valve into said closed position in response to said second signal to permit said inspiration to take place with constant compliance.

2. The ventilating device of claim 1, said reservoir means including: a branch line connected into said fresh gas line and a balloon-like expansion device connected to said branch line; and, said level sensing means being a pressure sensor connected to said branch line.

3. A ventilating apparatus comprising:

a closed breathing circuit for supplying fresh gas to a patient with said fresh gas containing gaseous components needed for ventilating the patient;

a ventilating device and pump unit connected to said breathing circuit and moving through inspirational and expirational strokes for maintaining the circulation of respirating gas in said breathing circuit;

a fresh gas line connected to said breathing circuit for conducting said fresh gas into said breathing circuit;

a metering unit for metering said fresh gas to said fresh gas line;

means for providing constant compliance during said inspiration, said means including a cutoff valve mounted in said fresh gas line between said breathing circuit and said metering unit so as to be downstream of said metering unit;

said cutoff valve being switchable between a closed position wherein said fresh gas line is cut off from said breathing circuit and an open position wherein said fresh gas line is open to said breathing circuit;

changeable volume reservoir means connected into said fresh gas line downstream of said metering unit and upstream of said cutoff valve for receiving said fresh gas therein when said cutoff valve is in said closed position;

level sensing means disposed at said reservoir means for sensing the level of fresh gas in said reservoir means and for providing an actual value signal indicative of said level;

a controller connected to said level sensing means for receiving said actual value signal and comparing said actual value signal to a pregiven desired value signal and for cutting off the supply of said fresh gas via said metering unit when the level of fresh gas in said reservoir means corresponds to said desired value signal;

means connected to said pumping device and pump unit for determining the beginning and end of said expirational stroke and for providing respective first and second electrical signals indicative of said beginning and said end of said expirational stroke; and, said controller being connected to said cutoff valve for electrically switching said cutoff valve into said open position in response to said first signal so as to permit said reservoir means to supply fresh gas stored therein to said breathing circuit in a quantity sufficient to replace the respirating gas consumed by the patient and/or lost because of possible leaks in the apparatus and to then switch said cutoff valve into said closed position in response to said second signal to permit said inspiration to take place with constant compliance.

4. A ventilating apparatus comprising:

a semi-closed breathing circuit for supplying fresh gas to a patient with said fresh gas containing gaseous components needed for ventilating the patient;

a pump unit connected into said breathing circuit for maintaining the circulation of respirating gas in said breathing circuit;

a fresh gas line connected to said breathing circuit for conducting said fresh gas into said breathing circuit;

a metering unit for metering said fresh gas to said fresh gas line;

means for providing constant compliance during said inspiration, said means including a cutoff valve mounted in said fresh gas line between said breathing circuit and said metering unit so as to be downstream of said metering unit;

said cutoff valve being switchable between a closed position wherein said fresh gas line is cut off from said breathing circuit and an open position wherein said fresh gas line is open to said breathing circuit;

changeable volume reservoir means connected into said fresh gas line downstream of said metering unit and upstream of said cutoff valve for receiving said fresh gas therein when said cutoff valve is in said closed position;

pressure measuring means connected to said pump unit for sensing the pressure of said respirating gas in said breathing circuit and for providing an actual value signal indicative of said pressure;

a controller for receiving said actual value signal and comparing said actual value signal to a pregiven desired value signal indicative of a predetermined pressure limit;

said cutoff valve being electrically switchable by said controller from said closed position wherein said inspiration takes place with constant compliance into said open position so as to permit said reservoir means to supply fresh gas stored therein to said breathing circuit in a quantity sufficient to replace the respirating gas consumed by the patient and/or lost because of possible leaks in the apparatus;

a relief valve connected to said breathing circuit and being switchable between a closed position and an open position for venting respirating gas to the ambient; and, said controller being connected to said relief valve for switching the latter into said open position to vent a portion of said respirating gas to the ambient when said pressure limit is exceeded.

* * * * *